United States Patent [19]
Drent et al.

US005166116A

[11] Patent Number: 5,166,116
[45] Date of Patent: Nov. 24, 1992

[54] CARBONYLATION CATALYST SYSTEM

[75] Inventors: Eit Drent; Petrus H. M. Budzelaar; Willem W. Jager; Johan Stapersma, all of Amsterdam, Netherlands

[73] Assignee: Shell Oil Company, Houston, Tex.

[21] Appl. No.: 650,537

[22] Filed: Feb. 5, 1991

[30] Foreign Application Priority Data

Feb. 5, 1990 [GB] United Kingdom ................. 9002491

[51] Int. Cl.$^5$ ............................................ B01J 31/02
[52] U.S. Cl. .................................... 502/167; 502/162
[58] Field of Search ................................. 502/167, 162

[56] References Cited

U.S. PATENT DOCUMENTS 4,414,409 11/1983 Waller ................................. 560/233

FOREIGN PATENT DOCUMENTS 0227160 12/1986 European Pat. Off. .

Primary Examiner—Patrick P. Garvin
Assistant Examiner—Brent M. Peebles

[57] ABSTRACT

A carbonylation catalyst system, which comprises:
a) a source of a Group VIII metal;
b) a source of a phosphine having an aromatic substituent containing an imino nitrogen atom;
c) a source of protons; and
d) a source of an alkylsulfonate anion, and the use of such a catalyst system in the carbonylation of an acetylenically or olefinically unsaturated compound.

7 Claims, No Drawings

CARBONYLATION CATALYST SYSTEM

FIELD OF THE INVENTION

The present invention relates to a novel catalyst system comprising a source of a Group VIII metal, a phosphine and a protonic acid and to the use of the catalyst system in the carbonylation of olefinically and acetylenically unsaturated compounds.

BACKGROUND OF THE INVENTION

Catalyst systems comprising a source of a Group VIII metal, a phosphine and a protonic acid are known for use in the carbonylation of acetylenically and olefinically unsaturated compounds. One type of catalyst system which has been disclosed comprises a source of a Group VIII metal, a pyridyl phosphine and a protonic acid.

European Patent Nos. A1-0259914 and EP-A1-0305012 discloses catalyst systems comprising a palladium compound, a pyridyl phosphine, an acid and a quinone and their use in the carbonylation of olefins to afford polymers. The examples illustrate the use of para-toluenesulfonic acid as the protonic acid.

European Patent No. A1-0282142 discloses the use of catalyst systems comprising a palladium compound, a pyridyl phosphine and a protonic acid in the carbonylation of olefins with hydroxyl-containing compounds. The examples illustrate the use of para-toluenesulfonic acid as the protonic acid.

European Patent No. A1-0271144 discloses the use of a catalyst system comprising a palladium compound, a pyridyl phosphine and a protonic acid in the carbonylation of acetylenes with hydroxyl-containing compounds. The examples illustrate the use of para-toluene sulfonic acid or benzene phosphoric acid as the protonic acid.

The Applicants have found that catalyst systems exemplified in European Patent No. A1-0271144 are poorly tolerant towards the presence of allene, which is a common impurity of unsaturated hydrocarbon compounds, especially acetylenes.

It has now been found that catalyst systems comprising a palladium compound, a pyridyl phosphine and an alkylsulphonic acid have outstandingly high activity in the carbonylation of acetylenically unsaturated compounds, and have improved tolerance towards the presence of allene.

SUMMARY OF THE INVENTION

The present invention therefore provides a carbonylation catalyst system, which comprises:
 a) a source of a Group VIII metal;
 b) a source of a phosphine having an aromatic substituent containing an imino nitrogen atom;
 c) a source of protons, and
 d) a source of an alkylsulphonate anion.

DESCRIPTION OF THE PREFERRED EMBODIMENTS

Catalyst systems according to the invention have been found to have higher activity in the carbonylation of acetylenically unsaturated compounds than catalyst systems comprising para-toluene sulfonic acid or benzene phoosphoric acid. Catalyst systems according to the invention have also been found to have greater tolerance towards allene.

The catalyst system used in the process according to the invention comprises a source of a Group VIII metal. The source of a Group VIII metal may be the metallic element. However, the source of the Group VIII metal is preferably a compound of the Group VIII metal.

Examples of Group VIII metals are iron, cobalt, nickel, ruthenium, rhodium, palladium, iridium and platinum.

The catalyst system according to the invention preferably comprises a source of a palladium compound.

Examples of compounds of Group VIII metals include salts, for example salts of nitric acid; sulfuric acid; sulfonic acids, for example an alkylsulfonic acid; carboxylic acids such as alkane carboxylic acids having not more than 12 carbon atoms, e.g. acetic acid; and hydrohalic acids. Since halide ions can be corrosive, salts of hydrohalic acids are not preferred. Other examples of compounds of Group VIII metals include complexes, such as complexes with acetylacetonate, phosphines and/or carbon monoxide. For example the compound of a Group VIII metal may be palladium acetylacetonate, tetrakis-triphenylphosphinepalladium, bis-tri-o-tolylphosphinepalladium acetate, bis-diphenyl-2-pyridylphosphinepalladium acetate, tetrakis-diphenyl-2-pyridylphosphinepalladium, bis-di-o-tolylpyridyl-phosphinepalladium acetate, or bis-diphenylpyridyl-phosphinepalladium sulfate.

The catalyst system used in the process according to the invention further comprises a source of a phosphine having an aromatic substituent which contains an imino nitrogen atom. The source of a phosphine is conveniently the phosphine itself, or an acid addition salt of the phosphine.

As used herein, the term "imino nitrogen atom" means a nitrogen atom which may be represented in the structural formula of the aromatic substituent containing it by the formula

For example, if the aromatic substituent is a pyridyl group, the structural formula of the aromatic substituent is

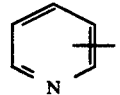

The phosphine preferably comprises one or two phosphorus atoms. Each phosphorus atom has three substituents. At least one of these substituents is an aromatic substituent which contains an imino nitrogen atom. The remaining substituents are preferably selected from optionally substituted aliphatic and aromatic hydrocarbyl groups. When the phosphine comprises more than one phosphorus atom, it is possible for one substituent to be shared by more than one phosphorus atom, as for example in

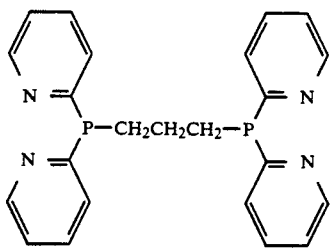

The aromatic substituent which contains an imino nitrogen is preferably a 6-membered ring containing one, two or three nitrogen atoms. The aromatic substituent may itself be optionally substituted.

When a substituent is said to be "optionally substituted" in this specification, unless stated otherwise the substituent may be unsubstituted or substituted by one or more substituents. Examples of suitable substituents include halogen atoms; alkyl groups; alkoxy groups; haloalkyl groups; haloalkoxy groups; acyl groups; acyloxy groups; amino groups; preferably alkyl or dialkylamino groups; hydroxy groups; nitrile groups; arylamino groups; and aromatic hydrocarbyl groups.

An aliphatic hydrocarbyl group is preferably an alkyl group, for example a $C_{1-4}$ alkyl group; or a cycloalkyl group, for example a $C_{3-6}$ cycloalkyl group.

An aromatic hydrocarbyl group is preferably a phenyl group.

A halogen atom, as such or in a haloalkyl group, is preferably a fluorine, chlorine or bromine atom.

An acyl group in an acyl, acyloxy or acylamino group is preferably a $C_{2-5}$ alkanoyl group such as acetyl.

Examples of aromatic substituents containing an imino nitrogen atom are pyridyl, pyrazinyl, quinolyl, isoquinolyl, pyrimidinyl, pyridazinyl, cinnolinyl, triazinyl, quinoxalinyl, and quinazolinyl. Preferred substituents are pyridyl and pyrimidyl.

An imino group in an aromatic substituent containing an imino nitrogen atom is preferably connected to a phosphorus atom through a single bridging carbon atom. For example, if the aromatic substituent is a pyridyl group, it is preferably connected through the carbon atom at the 2-position in the pyridyl group. Accordingly, examples of preferred aromatic substituents containing an imino nitrogen atom are 2-pyridyl; 2-pyrazinyl; 2-quinolyl; 1-isoquinolyl; 3-isoquinolyl; 2-pyrimidinyl; 3-pyridazinyl; 3-cinnolinyl; 2-triazinyl; 2-quinoxalinyl; and 2-quinazolinyl. 2-Pyridyl and 2-pyrimidyl are particularly preferred.

When the phosphine contains one phosphorus atom, it may conveniently be represented by the general formula

in which $R^1$ represents an aromatic substituent containing an imino nitrogen atom, and $R^2$ and $R^3$, which may be the same or different, represent a group $R^1$ or an optionally substituted aliphatic or aromatic hydrocarbyl group.

Examples of phosphines are:
bisphenyl-(2-pyridyl)phosphine,
bis(2-pyridyl)phenylphosphine,
tris(2-pyridyl)phosphine,
diphenyl(6-methoxy-2-pyridyl)phosphine,
bis(6-ethoxy-2-pyridyl)phenylphosphine,
bis(6-chloro-2-pyridyl)phenylphosphine,
bis(6-bromo-2-pyridyl)phenylphosphine,
tris(6-methyl-2-pyridyl)phosphine,
bis(6-methyl-2-pyridyl)phenylphosphine,
bisphenyl(6-methyl-2-pyridyl)phosphine,
bis(3-methyl-2-pyridyl)phenylphosphine,
bisphenyl(4,6-dimethyl-2-pyridyl)phosphine,
di(n-butyl)-2-pyridylphosphine,
dimethyl-2-pyridylphosphine,
methyl phenyl-2-pyridylphosphine,
n-butyl tert-butyl 2-pyridylphosphine,
n-butyl(4-methoxyphenyl) (2-pyridyl)phosphine, and
methyl di(2-pyridyl)phosphine.

Phosphines having an aromatic substituent containing an imino nitrogen atom are known compounds. They may conveniently be prepared by reacting a halophosphine or an alkali metal phosphide with an appropriate halo or alkali metal derivative of an aromatic compound containing an imino nitrogen atom. For example, diphenyl(6-methyl-2-pyridyl)phosphine may be prepared by reacting chlorodiphenylphosphine with 2-litho-6-methylpyridine.

The catalyst system used in the process according to the invention further comprises a source of protons. Conveniently the source of protons will be a protonic acid. However, the source of protons may be a compound which generates protons in situ. Preferably the source of protons is an alkylsulfonic acid, in which case it will also serve as a source of alkylsulfonate anions.

The source of an alkylsulfonate anion is preferably an alkylsulfonic acid, in which case it will also serve as a source of protons.

The alkyl group in the alkylsulphonate anion preferably has from 1 to 20, more preferably from 1 to 10, even more preferably from 1 to 6, especially from 1 to 4 carbon atoms. Examples of alkyl groups are methyl, ethyl, 1-propyl, 2-propyl, 1-butyl, 2-butyl, 2-methyl-1-propyl, 2-methyl-2-propyl(tertiary butyl), 1-pentyl, 1-hexyl, 1-heptyl, 1-octyl, 1-nonyl and 1-decyl.

The catalyst system used in the process according to the invention may be homogeneous or heterogeneous. Preferably, it is homogeneous.

The catalyst system according to the invention is constituted in a liquid phase. The liquid phase may conveniently be formed by one or more of the reactants with which the catalyst system is to be used. Alternatively, it may be formed by a solvent. It may also be formed by one of the components of the catalyst system.

The catalyst system according to the invention may be generated by any convenient method. Thus it may be prepared by combining a Group VIII metal compound, the phosphine and, if appropriate, an alkylsulfonic acid, in a liquid phase. Alternatively, it may be prepared by combining a Group VIII metal compound and an acid addition salt of the phosphine with an alkylsulfonic acid in a liquid phase. Alternatively, it may be prepared by combining a Group VIII metal compound which is a complex of a Group VIII metal with the phosphine and an alkylsulfonic acid, in a liquid phase.

The ratio of the number of moles of phosphine per gram atom of Group VIII metal is not critical. Preferably it is in the range of from 1 to 1000, more preferably from 2 to 500, especially from 10 to 100.

The ratio of the number of moles of phosphine per mole of protons is not critical. Preferably it is in the range of from 0.05 to 50, more preferably from 0.1 to 10, especially from 0.5 to 5. When the catalyst system is to be used to carbonylate an acetylenically unsaturated compound in the presence of an allenically unsaturated compound, preferably the number of moles of phosphine per mole of protons is at least 1, more preferably at least 1.2, even more preferably at least 1.4.

The number of moles of alkylsulfonate anion per mole of protons is not critical. Preferably it is in the range of from 0.1 to 100, more preferably from 0.5 to 50, especially from 0.75 to 5.

The catalyst system according to the invention preferably further comprises a tertiary amine promoter, especially when it is to be used to carbonylate an acetylenically unsaturated compound in the presence of an allenically unsaturated compound.

Examples of tertiary amines are trialkylamines, e.g. trimethylamine or triethylamine; N,N-dialkylanilines such as N,N-dimethylaniline, N,N-diethylaniline or p-methyl, N,N-dimethylaniline; and optionally substituted pyridines, especially pyridines substituted in the 2- and/or 6-position(s) such as 1,6-dichloropyridine; 1,6-dimethylpyridine and 1,6-ditert.butylpyridine. N,N-dialkylanilines are preferred as promoters.

The quantity of tertiary amine promoters used is not critical, but is preferably in the range of from 0.1 to 200 moles per mole of phosphine, more preferably from 0.5 to 100 moles, especially from 1 to 50 moles.

Accordingly, the invention further provides the use of a catalyst system as defined hereinbefore in the carbonylation of an acetylenically or olefinically unsaturated hydrocarbon.

According to another aspect, the invention provides a process for the carbonylation of an acetylenically or olefinically unsaturated compound, which comprises reacting an acetylenically or olefinically unsaturated compound with carbon monoxide in the presence of a catalyst system as defined above.

The acetylenically or olefinically unsaturated compound is preferably an asymmetric acetylene or olefin, most preferably an alpha acetylene or olefin.

An olefinically unsaturated compound is preferably a substituted or unsubstituted alkene or cycloalkene having from 2 to 30, preferably from 3 to 20 carbon atoms per molecule.

An acetylenically unsaturated compound is preferably a substituted or unsubstituted alkyne having from 2 to 20, especially from 3 to 10 carbon atoms per molecule.

The acetylenically or olefinically unsaturated compound may contain one or more acetylenic or olefinic bonds, for example one, two or three acetylenic or olefinic bonds.

An olefin or acetylene may be substituted by, for example, a halogen atom, a cyano group, an acyl group such as acetyl, an acyloxy group such as acetoxy, an amino group such as dialkylamino, an alkoxy group such as methoxy, a haloalkyl group such as trifluoromethyl, a haloalkoxy group such as trifluoromethoxy, an amido group such as acetamido, or a hydroxy group. Some of these groups may take part in the reaction, depending upon the precise reaction conditions. For example, lactones may be obtained by carbonylating certain acetylenically unsaturated alcohols, for example 3-butyn-1-ol, 4-pentyn-1-ol or 3-pentyn-1-ol. Thus 3-butyn-1-ol may be converted into α-methylene-γ-butyrolactone.

Examples of alkynes are: ethyne, propyne, phenylacetylene, 1-butyne, 2-butyne, 1-pentyne, 1-hexyne, 1-heptyne, 1-octyne, 2-octyne, 4-octyne, 1,7-octadiyne, 5-methyl-3-heptyne, 4-propyl-2-pentyne, 1-nonyne, benzylethyne and cyclohexylethyne.

Examples of alkenes are: ethene, propene, phenylethene, 1-butene, 2-butene, 1-pentene, 1-hexene, 1-heptene, 1-octene, 2-octene, 4-octene, cyclohexene and norbornadiene.

The acetylenically or olefinically unsaturated compound can be both an acetylene and an olefin, for example as in 3-methyl-but-3-ene-2-yne.

The unsaturated compound may be carbonylated alone or in the presence of other reactants, for example, hydrogen or a nucleophilic compound having a removable hydrogen atom. An example of a nucleophilic compound having a removable hydrogen atom is a hydroxyl-containing compound.

A hydroxyl-containing compound is preferably an alcohol, water or a carboxylic acid.

Any alcohol used may be aliphatic, cycloaliphatic or aromatic and may carry one or more substituents. The alcohol preferably comprises up to 20 carbon atoms per molecule. It may be, for example, an alkanol, a cycloalkanol or a phenol. One or more hydroxyl groups may be present, in which case several products may be formed, depending on the molar ratio of the reactants used.

Examples of alkanols include methanol, ethanol, 1-propanol, 2-propanol, 1-butanol, 2-butanol, 2-methylpropan-1-ol, and 2-methylpropan-2-ol.

Examples of phenols include phenol, alkylphenols, catechols, and 2,2-bis(4-hydroxyphenyl)propane.

Other examples of alcohols include polyvalent alcohols, in particular lower sugars such as glucose, fructose, mannose, galactose, sucrose, aldoxose, aldopentose, altrose, allose, talose, gulose, idose, ribose, arabonose, xylose, lyxose, erythrose or threose, cellulose, benzyl alcohol, 2,2-bis(hydroxymethyl)-1-butanol, stearyl alcohol, cyclohexanol, ethylene glycol, 1,2-propanediol, 1,4-butanediol, polyethyleneglycol, glycerol and 1,6-hexanediol.

The process according to the present invention can be carried out using a wide variety of carboxylic acids. For example, the carboxylic acids may be aliphatic, cycloaliphatic or aromatic and may carry one or more substituents, such as those named in connection with the acetylenically and olefinically unsaturated compounds.

Carboxylic acids preferably used in the process according to the invention include those containing up to 20 carbon atoms. One or more carboxylic acid groups may be present, thus allowing various products as desired, depending on the molar ratio of the reactants used. The carboxylic acids may, for example, be alkanecarboxylic acids or alkenecarboxylic acids. Examples of carboxylic acids are: formic acid, acetic acid, propionic acid, n-butyric acid, isobutyric acid, pivalic acid, n-valeric acid, n-caproic acid, caprylic acid, capric acid, lauric acid, myristic acid, palmitic acid, stearic acid, benzoic acid, o-phthalic acid, m-phthalic acid, terephthalic acid and toluic acid. Examples of alkenecarboxylic acids are acrylic acid, propiolic acid, methacrylic acid, crotonic acid, isocrotonic acid, oleic acid, maleic acid, fumaric acid, citraconic acid and mesaconic acid.

It will be appreciated that the unsaturated hydrocarbon and the hydroxyl-containing compound may be the same compound.

When an acetylenically unsaturated compound is reacted with water and carbon monoxide, an alpha,-beta-unsaturated carboxylic acid is formed. If an alcohol is used instead of water, an alpha,beta-unsaturated carboxylic ester is formed. If a carboxylic acid is used instead of water, an alpha,beta-unsaturated anhydride is formed. The alpha,beta-unsaturated product may undergo further reaction depending upon the reaction conditions employed.

It will be appreciated that the unsaturated hydrocarbon and the hydroxyl-containing compound may be the same compound.

It is not essential to use a separate solvent in the process according to the invention.

A large excess of the product or of one of the reactants, for example an alcohol, can often form a suitable liquid phase. In some cases, however, it may be desirable to use a separate solvent. Any inert solvent can be used for that purpose. Said solvent may, for example, comprise sulfoxides and sulfones, for example dimethylsulfoxide, diisopropylsulfone or tetrahydrothiophene-2,2-dioxide (also referred to as sulfolane), 2-methylsulfolane, 3-methylsulfolane, 2-methyl-4-butylsulfolane; aromatic hydrocarbons such as benzene, toluene, xylenes; esters such as methylacetate and butyrolactone; ketones such as acetone or methyl isobutyl ketone and ethers such as anisole, 2,5,8-trioxanone (also referred to as diglyme), diphenyl ether and diisopropyl ether, or an amide such as dimethylacetamide or N-methylpyrrolidone.

The process according to the present invention is conveniently effected at a temperature in the range of from 10° C. to 200° C., in particular from 20° C. to 100° C.

The process according to the invention is preferably effected at a pressure of from 1 to 70 bar. Pressures higher than 100 bar may be used, but are generally economically unattractive on account of special apparatus requirements.

The molar ratio of the hydroxyl-containing compound to the acetylenically unsaturated hydrocarbon may vary between wide limits and generally lies within the range of 0.01:1 to 100:1.

The quantity of the Group VIII metal is not critical. Preferably, quantities are used within the range of $10^{-7}$ to $10^{-1}$ gram atom Group VIII metal per mol of acetylenically unsaturated compound.

Catalyst systems according to the invention have been found to perform particularly well in the carbonylation of acetylenically unsaturated compounds in the presence of allenically unsaturated compounds.

When present, the allenically unsaturated compound is preferably present in an amount in the range of from 0.003 to 10 moles per mole of acetylenically unsaturated compound, more preferably from 0.01 to 5.

The carbon monoxide required for the process according to the present invention may be used in a practically pure form or diluted with an inert gas, for example nitrogen. The presence of more than small quantities of hydrogen in the gas stream is undesirable on account of the hydrogenation of the unsaturated hydrocarbon which may occur under the reaction conditions. In general, it is preferred that the quantity of hydrogen in the gas stream supplied is less than 5 vol %.

The invention will now be illustrated by the following Preparations and Examples which are illustrative and which are not intended to be construed as limiting the invention.

PREPARATION 1

Preparation of diphenyl-(6-methyl-2-pyridyl)-phosphine

All manipulations were carried out in an inert atmosphere (nitrogen or argon). Solvents were dried and distilled prior to use. 36 ml of a 1.6M n-butyllithium solution in hexane was added to 40 ml diethyl ether, and the mixture was cooled to −40° C. To the stirred mixture was added in the course of 20 minutes a solution of 10 g 2-bromo-6-methylpyridine in 15 ml diethyl ether; during this addition, the temperature was kept at −40° C. After the addition, the temperature was raised to −5° C., kept there for 5 minutes, and then lowered again to −40° C. A solution of 12.8 g chlorodiphenylphosphine in 15 ml diethyl ether was added in the course of 15 minutes to the stirred mixture. After the addition, the mixture was warmed to room temperature, the solvents were removed in vacuo, and 50 ml water and 50 ml dichloromethane were added. After 5 minutes of vigorous stirring, the dichloromethane layer was separated. The water layer was extracted with two 50 ml portions of dichloromethane, the organic reactions were combined, and the solvent removed in vacuo. The residue was crystallized from toluene/hexane to afford 12 g (75%) of diphenyl-(6-methyl-2-pyridyl)-phosphine as off-white crystals. The product was characterized by $^{31}$P NMR: $\delta_p = -5.6$ ppm.

PREPARATION 2

Preparation of diphenyl-(3-methyl-2-pyridyl)-phosphine

This compound was prepared as described in Preparation 1, but using 10.0 g 2-bromo-3-methylpyridine instead of the 2-bromo-6-methylpyridine. It was characterized by $^{31}$P NMR: $\delta_p = -8.1$ ppm.

PREPARATION 3

Preparation of phenyl-bis(6-methyl-2-pyridyl)-phosphine

This compound was prepared as described in Preparation 1, but using 5.2 g of phenyldichlorophosphine instead of the chlorodiphenylphosphine. It was characterized by $^{31}$P NMR: $\delta_p = -5.1$ ppm.

PREPARATION 4

Preparation of tris(6-methyl-2-pyridyl)-phosphine

This compound was prepared as described in Preparation 1, but using 2.7 g of phosphorus trichloride instead of the chlorodiphenylphosphine. It was characterized by $^{31}$P NMR: $\delta_p = -3.8$ ppm.

PREPARATION 5

Preparation of diphenyl-(4,6-dimethyl-2-pyridyl)-phosphine

This compound was prepared as described in Preparation 1, but using 10.8 g of 2-bromo-4,6-dimethylpyridine instead of the 2-bromo-6-methylpyridine. It was characterized by $^{31}$P NMR: $\delta_p = -5.6$ ppm.

PREPARATION 6

Preparation of diphenyl-(6-methoxy-2-pyridyl)-phosphine 2.7 g Sodium was added to 100 ml liquid ammonia at −80° C., and then 15.2 g of triphenylphosphine was added in 6 portions with stirring. The solution was slowly warmed to −40° C., kept at that temperature for 30 min, and then cooled again to −80° C. Then, 3.1 g ammonium chloride was added to the stirred solution, followed by 10.9 g of 2-bromo-6-methoxypyridine in three portions. The cooling bath was removed and the ammonia was allowed to evaporate. The residue was worked up with water/dichloromethane as described in Preparation 1. Crystallization from hexane afforded 7 g of a somewhat impure product (characterized by $^{31}P$ NMR: $\delta_p = -4.4$ ppm) which was used as such in the following Examples.

PREPARATION 7

Preparation of di(n-butyl)-2-pyridyl phosphine

To a magnetically stirred solution of 2.5 g phenyl(2-pyridyl)$_2$P in 20 mol tetrahydrofuran, cooled to −80° C., was added in the course of 10 min 5.9 ml of a 1.6M solution of n-butylLi in hexane. The resulting deep-red solution was allowed to warm to room temperature, and analysis of the solution by $^{31}P$ NMR showed it to contain the phosphide (n-butyl)(2-pyridyl)-PLi as the only phosphorus-containing compound ($\delta_p = -16.3$ ppm).

The solution was cooled to −40° C. and a solution of 1.3 g 1-bromobutane in 10 ml tetrahydrofuran was added. The mixture was again warmed to room temperature, the solvents were removed in vacuo, and 25 ml of diethylether and 10 ml of water were added. After 10 min of stirring, the organic layer was separated and the water layer was extracted with 10 ml of ether. The organic layers were combined and the solvent was removed in vacuo (66 Pa). The resulting light-yellow liquid was analyzed by $^1H$, $^{13}C$ and $^{31}P$ NMR and shown to consist of a 1:1 (molar ratio) mixture of 2-phenylpyridine and (n-butyl)$_2$(2-pyridyl)P ($\delta_p = -19.5$ ppm).

PREPARATION 8

Preparation of dimethyl 2-pyridyl phosphine and methylphenyl-2-pyridyl phosphine The method of Preparation 7 was repeated, except that a 1.6M solution of methylLi in diethylether was used instead of the n-butylLi solution, and 1.3 g iodomethane instead of the bromobutane. The reaction product was a mixture of (methyl)$_2$ 2-pyridyl)P, methyl phenyl 2-pyridylP and 2-phenyl pyridine in the approximate ratio 70:30:60, from which the (methyl)$_2$(2-pyridyl)P was isolated by distillation.

The physical characteristics of the products were $\delta_p = -41.2$ ppm (dimethyl-2-pyridylphosphine) and $\delta_p = -24.1$ ppm (methylphenyl-2-pyridylphosphine).

PREPARATION 9

Preparation of n-butyl tert-butyl 2-pyridyl phosphine

The method of Preparation 7 was repeated, except that 5.6 ml of a 1.7M solution of t-butylLi in pentane was used instead of the n-butylLi solution. The final product was identified as n-butyl t-butyl 2-pyridylP by NMR analysis ($\delta_p = 7.4$ ppm).

PREPARATION 10

Preparation of dimethyl 2-pyridylphosphine

The method of Preparation 8 was repeated, except that 1.91 g of methyl(2-pyridyl)$_2$P and only 0.7 g iodomethane were used. Workup as described in Example 1 afforded dimethyl 2-pyridyl phosphine, which was further purified by distillation (65% yield). ($\delta_p = -41.2$ ppm).

PREPARATION 11

Preparation of n-butyl(4-methoxyphenyl)(2-pyridyl)phosphine

All manipulations were carried out in an inert atmosphere (nitrogen or argon). Solvents were dried and distilled prior to use. 18 ml of a 1.6M n-butyllithium solution in hexane was added to 30 ml diethyl ether, and the mixture was cooled to −40° C. To the stirred mixture was added in the course of 20 minutes a solution of 4.6 g of 2-bromopyridine in 15 ml diethyl ether; during this addition, the temperature was kept at −40° C. After the addition, the temperature was raised to −5° C., kept there for 5 minutes, and then lowered again to −40° C. The resulting solution was added to a cooled (−40° C.) solution of 7.6 g 4-methoxyphenyl-bis(2-pyridyl)-phosphine in 30 ml THF. The mixture was warmed to room temperature. After stirring for 10 minutes, the solvents were removed in vacuo. Water (25 ml) and dichloromethane (25 ml) were added. After 5 minutes of vigorous stirring, the dichloromethane layer was separated. The water layer was extracted with two 25-ml portions of dichloromethane, the organic fractions were combined, and the solvent removed in vacuo. The residue was distilled, giving 4.7 g (60%) of (n-butyl)(4-methoxyphenyl)(2-pyridyl)phosphine as a yellowish liquid. The product was characterized by $^{31}P$ NMR: $\delta_p = -14.9$ ppm.

In this experiment, n-butyllithium is believed to react with 2-bromopyridine to afford a mixture of n-butylbromide and 2-pyridyllithium. Then the 2-pyridyllithium reacts with 4-methoxy-bis(2-pyridyl)phosphine to afford 4-methoxyphenyl(2-pyridyl)lithium phosphide (and 2,2'-bipyridine). The lithium phosphide then reacts with n-butylbromide to afford (n-butyl)(4-methoxyphenyl)(2-pyridyl)phosphine.

PREPARATION 12

Preparation of methyl di(2-pyridyl)phosphine

All manipulations were carried out in an inert atmosphere (nitrogen or argon). Solvents were dried and distilled prior to use. 36 ml of a 1.6M n-butyllithium solution in hexane was added to 40 ml diethyl ether, and the mixture was cooled to −40° C. To the stirred mixture was added in the course of 20 minutes a solution of 9.2 g 2-bromopyridine in 15 ml diethyl ether; during this addition, the temperature was kept at −40° C. After the addition, the temperature was raised to −5° C., kept there for 5 minutes, and then lowered again to −40° C. A solution of 3.4 g methyldichlorophosphine in 15 ml diethyl ether was added to the stirred mixture. After the addition, the mixture was warmed to room temperature, the solvents were removed in vacuo, and 50 ml water and 50 ml dichloromethane were added. After 5 minutes of vigorous stirring, the dichloromethane layer was separated. The water layer was extracted with two 50-ml portions of dichloromethane, the organic fractions were combined, and the solvent removed in vacuo. The residue was distilled, giving 4.0 g (68%) of methyl-bis(2-pyridyl)phosphine as a yellowish liquid. The product was characterized by $^{31}P$ NMR: $\delta_p = -20.5$ ppm.

EXAMPLE 1

A 300 ml magnetically-stirred stainless steel autoclave was successively filled with 0.025 mmol palladium(II)acetate, 1 mmol bisphenyl (6-methyl-2-pyridyl) phosphine, 2 mmol 2-methyl-2-propylsulfonic acid, 30 ml N-methylpyrrolidone as solvent and 30 ml methanol. Air was then evacuated from the autoclave, and then 30 ml propyne containing 0.2% allene was added. Carbon monoxide was then added to a pressure of 60 bar. The autoclave was then sealed and heated to a temperature of 60° C. After a reaction time of 0.15 hours at 60° C., a sample of the contents of the autoclave was analyzed by gas liquid chromatography. From the results of the analysis, the selectivity to methylmethacrylate was calculated to be 99.95%, and the mean conversion rate was calculated to be 100,000 mol propyne/gram atom Pd/hour.

EXAMPLES 2 TO 15 AND COMPARATIVE EXAMPLES A TO H

The method of Example 1 was repeated using differing acids, solvents and phosphines, and differing amounts of allene in the propyne. The results are summarized in Table 1.

The results demonstrate that catalyst systems comprising an alkylsulfonate anion are substantially more active than catalyst systems comprising other anions, including para-toluenesulfonate and benzenephosphonate anions. The results also demonstrate that the activity of the catalyst is reduced as the allene content of the propyne is increased, and that this reduction of activity may be limited by selecting an amide such as N-methylpyrrolidone or N,N-dimethylacetamide as reaction solvent and/or by increasing the molar ratio of phosphine to acid.

TABLE 1

Carbonylation of Propyne and Methanol to give methyl methacrylate

| Example | Ligand (mmol) | Acid (mmol) | Solvent | % allene | Temp (°C.) | Selectivity (%) | Mean Conversion rate (mol propyne/gat.Pd/hr) |
|---|---|---|---|---|---|---|---|
| 1 | 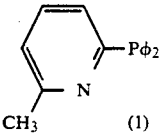 (1) | $(CH_3)_3CSO_3H$ (2) | NMP | 0.2 | 60 | 99.95 | 100,000 |
| 2 | 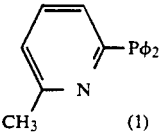 (1) | $(CH_3)SO_3H$ (2) | NMP | 0.2 | 60 | 99.95 | 50,000 |
| A | 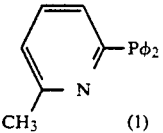 (1) | $CH_3$—⌬—$SO_3H$ (2) | NMP | 0.2 | 60 | 99.95 | 40,000 |
| B | 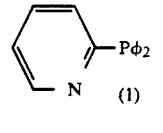 (1) | $CH_3$—⌬—$SO_3H$ (2) | NMP | 0.2 | 60 | 98.9 | 40,000 |
| C | 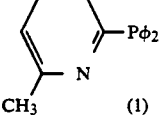 (1) | ⌬—$PO_3H_2$ (10) | NMP | 0.2 | 60 | 99.95 | 6,000 |
| D | 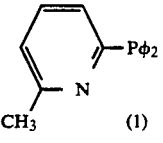 (1) | $CF_3SO_3H$ (2) | NMP | 0.2 | 60 | 99.95 | 16,000 |
| E | 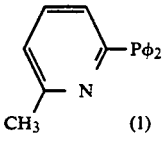 (1) | $CF_3COOH$ (10) | NMP | 0.2 | 60 | 99.95 | 14,000 |

TABLE 1-continued

Carbonylation of Propyne and Methanol to give methyl methacrylate

| Example | Ligand (mmol) | Acid (mmol) | Solvent | % allene | Temp (°C.) | Selectivity (%) | Mean Conversion rate (mol propyne/ gat.Pd/hr) |
|---|---|---|---|---|---|---|---|
| 3 | 2-(diphenylphosphino)-6-methylpyridine (1) | $(CH_3)_3CSO_3H$ (2) | NMP | 0.4 | 60 | 99.95 | 10,000 |
| 4 | 2-(diphenylphosphino)-6-methylpyridine (1) | $(CH_3)_3CSO_3H$ (2) | NMP | 0.4 | 70 | 99.95 | 50,000 |
| 5 | 2-(diphenylphosphino)-6-methylpyridine (1) | $CH_3SO_3H$ (2) | DMA | 0.4 | 60 | 99.95 | 45,000 |
| F | 2-(diphenylphosphino)pyridine (1) | $CH_3$-C$_6H_4$-$SO_3H$ (2) | NMP | 0.4 | 60 | 98.9 | 4,000 |
| 6 | 2-(diphenylphosphino)-6-methylpyridine (1) | $CH_3SO_3H$ (2) | MMA | 0.4 | 60 | 99.95 | 5,000 |
| 7 | 2-(diphenylphosphino)pyridine (1) | $CH_3SO_3H$ (2) | MMA | 0.4 | 60 | 98.9 | 7,000 |
| G | 2-(diphenylphosphino)-6-methylpyridine (1) | $CH_3$-C$_6H_4$-$SO_3H$ (2) | MMA | 0.4 | 60 | 99.94 | 1,000 |
| 8 | 2-(diphenylphosphino)-3-methylpyridine (1) | $CH_3SO_3H$ (2) | NMP | 0.4 | 70 | 99.2 | 12,000 |
| 9 | 2-(diphenylphosphino)-4-methylpyridine (1) | $CH_3SO_3H$ (2) | NMP | 0.4 | 70 | 98.8 | 8,000 |
| 10 | 2-(diphenylphosphino)-4-methyl-6-methylpyridine (1) | $CH_3SO_3H$ (2) | NMP | 0.4 | 70 | 99.9 | 11,000 |

TABLE 1-continued

Carbonylation of Propyne and Methanol to give methyl methacrylate

| Example | Ligand (mmol) | Acid (mmol) | Solvent | % allene | Temp (°C.) | Selectivity (%) | Mean Conversion rate (mol propyne/ gat.Pd/hr) |
|---|---|---|---|---|---|---|---|
| 11 | 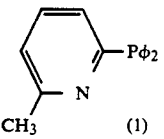 6-methyl-2-pyridyl-Pφ₂ (1) | CH₃SO₃H (2) | NMP | 0.4 | 80 | 99.85 | 3,500 |
| 12 | 2-pyridyl-Pφ₂ (3) | CH₃SO₃H (2) | MMA | 0.4 | 60 | 98.9 | 90,000 |
| 13 | 6-methyl-2-pyridyl-Pφ₂ (3) | CH₃SO₃H (2) | MMA | 0.4 | 60 | 99.94 | 210,000 |
| H | 2-pyridyl-Pφ₂ (3) | CH₃-C₆H₁₀-SO₃H (2) | MMA | 0.4 | 60 | 98.9 | 8,000 |
| 14 | 6-methyl-2-pyridyl-Pφ₂ (3) | (CH₃)₃CSO₃H (2) | MMA | 2.5 | 40 | 99.9 | 4,000 |
| 15 | 6-methyl-2-pyridyl-Pφ₂ (3) | (CH₃)₃CSO₃H (2) | MMA | 2.5 | 60 | 99.9 | 6,000 |

Key
NMP N-methylpyrrolidone
DMA N,N-dimethylacetamide
MMA Methylmethacrylate
φ Phenyl group

EXAMPLE 16

A 300 ml magnetically-stirred stainless steel autoclave was successively filled with 0.025 mmol palladium(II)acetate, 1 mmol bisphenyl (6-methyl-2-pyridyl) phosphine, 2 mmol 2-methyl-2-propylsulfonic acid, 30 ml methyl methacrylate as solvent, 30 ml methanol and 10 mmol dimethylaniline as promoter. Air was then evacuated from the autoclave, and then 30 ml propyne containing 0.4% allene was added. Carbon monoxide was then added to a pressure of 60 bar. The autoclave was then sealed and heated to a temperature of 60° C. After a reaction time of 0.1 hour at 60° C., a sample of the contents of the autoclave was analyzed by gas liquid chromatography. From the results of the analysis, the selectivity to methyl methacrylate was calculated to be 99.94% and the mean conversion rate was calculated to be 90,000 mol propyne/gram atom Pd/hour.

EXAMPLES 17 TO 23

The method of Example 16 was repeated using differing promoters and acids, and differing amounts of allene in the propyne. The results are summarized in Table 2.

The results demonstrate that the inhibitory effect of allene on the catalyst can be counteracted by using catalytic quantities of tertiary amines as promoters.

TABLE 2

Carbonylation of Propyne and Methanol to give methyl methacrylate

| Example | Ligand (mmol) | Acid (mmol) | Solvent | Promoter (mmol) | % allene | Temp (°C.) | Selectivity (%) | Mean Conversion rate (mol propyne/gat.Pd/hr) |
|---|---|---|---|---|---|---|---|---|
| 16 | 6-methyl-2-(diphenylphosphino)pyridine (1) | CH$_3$SO$_3$H (2) | MMA | N,N-dimethylaniline (10) | 0.4 | 60 | 99.94 | 90,000 |
| 17 | 2-(diphenylphosphino)pyridine (1) | CH$_3$SO$_3$H (2) | MMA | 4-methyl-N,N-dimethylaniline (2.5) | 0.4 | 60 | 99.0 | 67,000 |
| 18 | 6-methyl-2-(diphenylphosphino)pyridine (1) | CH$_3$SO$_3$H (2) | MMA | 4-methyl-N,N-dimethylaniline (20) | 0.4 | 60 | 99.94 | 18,000 |
| 19 | 6-methyl-2-(diphenylphosphino)pyridine (1) | CH$_3$SO$_3$H (2) | MMA | 2,6-di-tert-butylpyridine (2.5) | 0.4 | 60 | 99.9 | 30,000 |
| 20 | 6-methyl-2-(diphenylphosphino)pyridine (1) | CH$_3$SO$_3$H (2) | MMA | 3,4-dimethylpyridine (2.5) | 0.4 | 60 | 99.9 | 9,000 |
| 21 | 6-methyl-2-(diphenylphosphino)pyridine (1) | CH$_3$SO$_3$H (2) | MMA | 2,6-dichloropyridine (2.5) | 0.4 | 60 | 99.9 | 15,000 |
| 22 | 6-methyl-2-(diphenylphosphino)pyridine (1) | CH$_3$SO$_3$H (2) | MMA | 4-methyl-N,N-dimethylaniline (10) | 2.0 | 60 | 99.9 | 7,000 |
| 23 | 6-methyl-2-(diphenylphosphino)pyridine (3) | (CH$_3$)$_3$CSO$_3$H (2) | MMA | 4-methyl-N,N-dimethylaniline (10) | 7.0 | 45 | 99.9 | 6,000 |

Key
MMA Methylmethacrylate
φ Phenyl group

We claim:
1. A carbonylation system, which comprises:
   a) a compound of a Group VIII metal;
   b) a phosphine having an aromatic substituent containing an imino nitrogen atom;
   c) protons; and
   d) an alkylsulfonate anion.

2. The catalyst system of claim 1 wherein the Group VIII metal is palladium.

3. The catalyst system of claim 2 wherein an imino group in an aromatic substituent an imino nitrogen atom is linked to a phosphorus atom through a single bridging carbon atom.

4. The catalyst system of claim 3 wherein the phosphine is a 2-pyridyl, 2-pyrimidyl or 2-triazinylphosphine.

5. The catalyst system of claim 1 wherein the alkylsulfonate anion has from 1 to 6 carbon atoms.

6. The catalyst system of claim 1 wherein the number of moles of phosphine per gram atom of Group VIII metal is in the range of from 2 to 500, the number of moles of phosphine per mole of protons is in the range of from 0.5 to 50, and the number of moles alkylsulfonate anion per mole of protons is in the range of from 0.5 to 50.

7. The catalyst system of claim 1 wherein said catalyst system further comprises a tertiary amine as promoter.

* * * * *